United States Patent

Sheridan et al.

Patent Number: 5,127,830
Date of Patent: Jul. 7, 1992

[54] DENTAL INSTRUMENT SHIELD

[76] Inventors: John J. Sheridan, 1401 Lake St. Unit E-8, Metairie, La. 70005; Maureen C. Sheridan, 919 Monrovia, Shreveport, La. 71106; Richard F. Finger, 502 N. Van Buren, East Dundee, Ill. 60118

[21] Appl. No.: 550,347

[22] Filed: Jul. 9, 1990

[51] Int. Cl.$^5$ ............................................. A61G 15/00
[52] U.S. Cl. ........................................ 433/77; 433/79
[58] Field of Search ........................... 433/77, 79, 49; 312/209

[56] References Cited

U.S. PATENT DOCUMENTS

| | | | |
|---|---|---|---|
| 4,306,862 | 12/1981 | Knox | 433/77 |
| 4,321,913 | 3/1982 | Maluta et al. | 312/209 |
| 4,618,326 | 10/1986 | Schmidt et al. | 433/79 |
| 4,730,880 | 3/1988 | Schmidt et al. | 312/209 |
| 4,834,357 | 5/1989 | Bodenmiller | 269/289 R |
| 4,952,146 | 8/1990 | Doty | 433/77 |

*Primary Examiner*—Gene Mancene
*Assistant Examiner*—Cindy A. Cherichetti
*Attorney, Agent, or Firm*—John M. Harrison

[57] ABSTRACT

A dental instrument shield for shielding medical or dental instruments, as well as industrial tools and equipment, which, due to position and configuration, may accidentally pierce or contact tissue and cause injury. In a preferred embodiment the dental instrument shield includes a curved, transparent, protective guard adjustably supported on parallel support rods mounted on an instrument support bar which is attached to a console or other supporting surface. An instrument tray may be mounted in adjustable relationship on the curved guard and the guard is designed to extend over the various handpieces containing dental instruments, to prevent accidental contact with the dental instruments. The various handpieces are typically removably supported in handpiece receptacles of various design for convenient access. The protective guard may alternatively be secured directly to a console or other supporting surface by means of a bracket or otherwise and may be shaped to partially and adjustably enclose one or more handpieces.

20 Claims, 2 Drawing Sheets

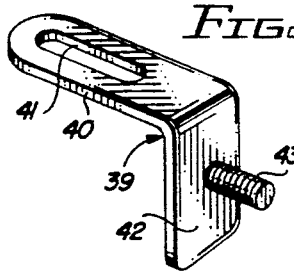
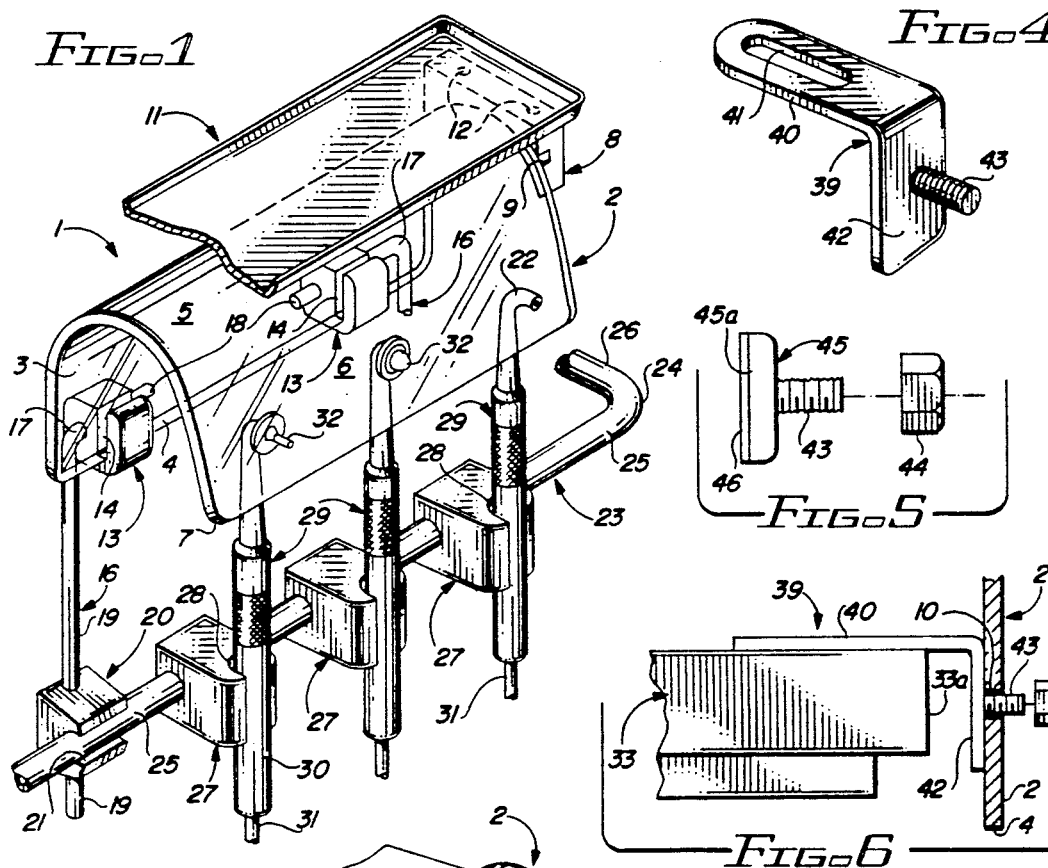
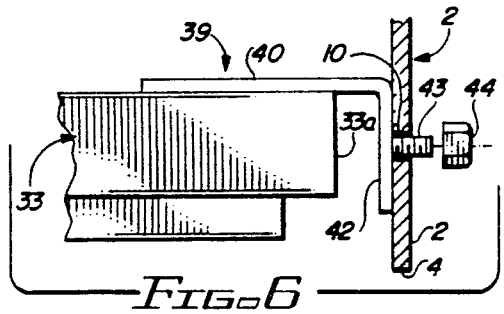
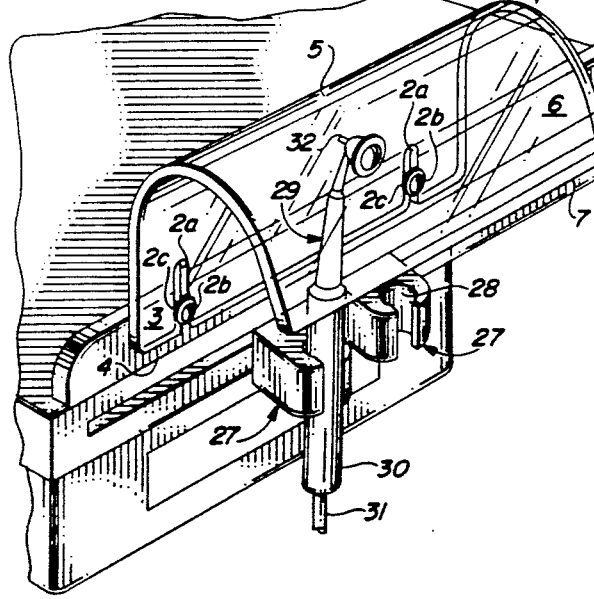
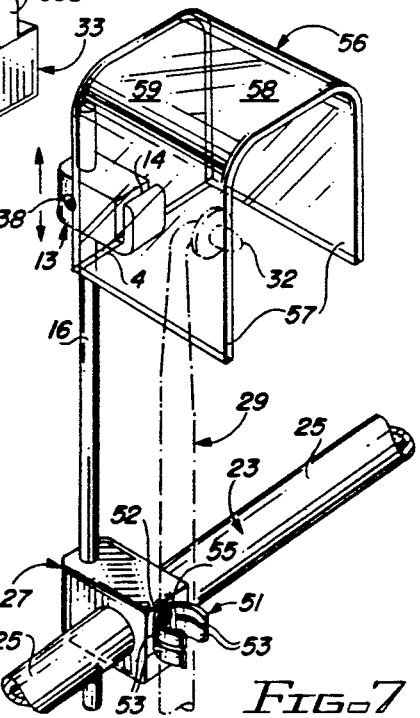

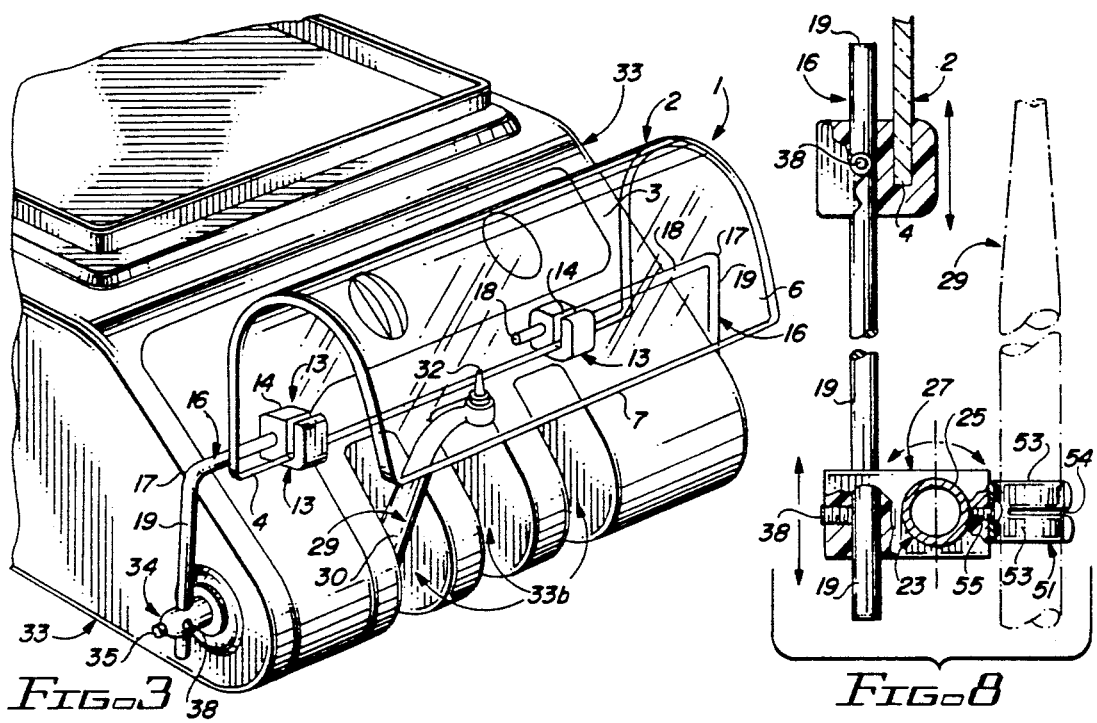
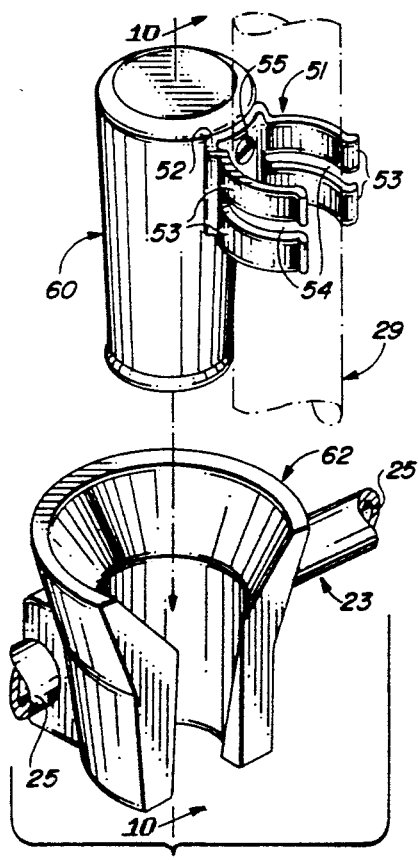
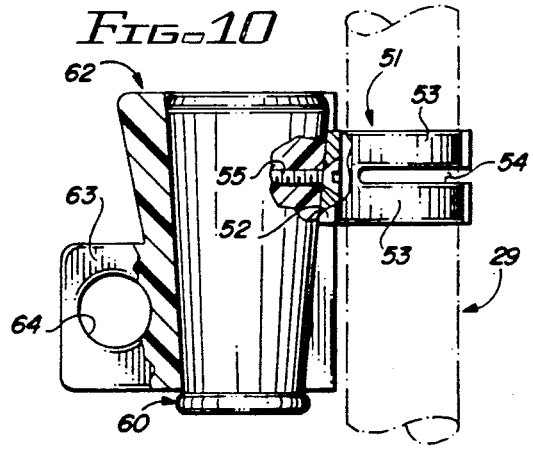
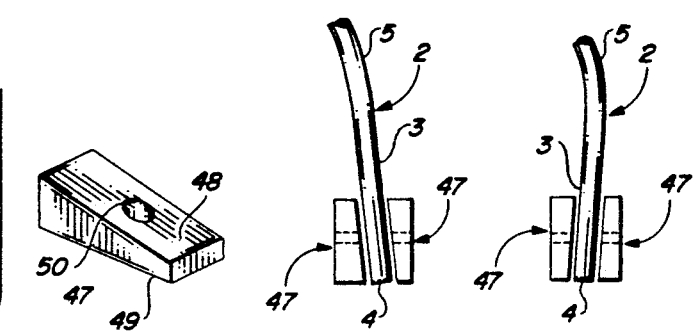

DENTAL INSTRUMENT SHIELD

BACKGROUND OF THE INVENTION

1. Field of the Invention

This invention relates to the shielding of dental instruments and dental handpieces, as well as industrial tools and equipment and more particularly, to a dental instrument shield which is designed to prevent the transfer of communicable diseases by shielding the various medical or dental instruments mounted on dental handpieces. These instruments may accidentally wound a dentist, dental technician or assistant or a patient due to normal handpiece position and location in the dental office. The dental instrument shield of this invention is characterized by a transparent or opaque guard of selected size, which, in a first preferred embodiment, is transparent and curved from front to rear and adjustably mounted on a pair of vertical support rods which are adjustably attached to a common support bar secured to a console or other fixture. Alternatively, the guard may be flat or angulated, depending upon the configuration of the instrument, tool or equipment to be protected. An instrument tray constructed of any desired material may be adjustably secured to the transparent guard for receiving various instruments used by the dentist or technician. The front portion of the guard extends over one or more handpieces to shield the various dental instruments mounted in the handpieces and prevent accidental contact between the dentist, technician or patient. The handpiece or handpieces are supported in handpiece receptacles of various designs.

Certain dental instruments such as dental drills, probes and other sharp tools may be incorporated in dental handpieces which are normally seated in receptacles in a dental console. These instruments may be contaminated with a patient's saliva, and often blood, during the course of normal dental procedures and since they are normally uncovered and exposed when not used, the instruments are capable of piercing tissue if the dentist's chairside assistant or patient inadvertently contacts them. The various drills, probes and other dental instruments are potentially lethal, since the blood residue may contain such viruses as hepatitis and AIDS.

While many different console designs have been developed for supporting handpieces containing various dental instruments, few, if any, of these consoles incorporate a guard feature for preventing inadvertent contact between the dental instruments and the dentist, the dental assistant or the patient. The nature of using conventional dental handpieces dictates that the handpieces be located within easy reach, readily available for use by the dentist and therefore unimpeded by any obstruction.

2. Description of the Prior Art

Various types of dental equipment and apparatus are known in the art. An early unitary dental apparatus is detailed in U.S. Pat. No. 2,261,036, dated Oct. 28, 1941, to O. H. Pieper. The Pieper dental apparatus includes a cabinet designed to enclose a handpiece and dental instrument, the door of which cabinet is secured in position by an elaborate system of pulleys and a counterweight to facilitate easy opening and closing. A "Dental Equipment Stand" is detailed in U.S. Pat. No. 3,280,458, dated Oct. 25, 1966, to H. U. Deeley, Jr., et al. The stand features various linkages and mechanisms to facilitate convenient access to various dental instruments attached thereto. Another "Dental Console " is detailed in U.S. Pat. No. 3,718,972, dated Mar. 6, 1973, to S. S. Fox, et al. The Fox et al. console includes a pair of doors which open to access a dental instrument tray which is mounted on drawer extensions, such that the tray can be extended a selected distance for easy access by a dentist or technician. U.S. Pat. No. 4,231,737, dated Nov. 4, 1980, to J. Groen, details an "Apparatus for Removably Supporting at Least One Medical, Particularly Dental Instrument, Such As A Dental Drill or the Like". The apparatus includes a box provided with a holder for containing one or more dental instruments and a supply tube connected to the box. A device for automatically retracting the tube at least partially into the box is also included. A "Priority System Dental Instrument Delivery" is detailed in U.S. Pat. No. 4,351,634, dated Sep. 28, 1982, to W. Rosenfeldt, which dental delivery unit includes a number of dental instruments in nests. Upon selection, a nest is extended and carries its instruments to the dentist's proximity. The selection is accomplished by a priority system and associated with each nest is a switch, the activation of which starts a selection period by the priority system. At the end of the selection period the nest corresponding to the last activated switch is extended by the priority system.

It is an object of this invention to provide a shield constructed of any desired material which is designed to prevent the transfer of communicable diseases by shielding various tools and equipment, including medical or dental instruments that, due to position and configuration, may accidentally contact or pierce tissue and cause injury.

Another object of the invention is to provide an adjustable, versatile dental instrument shield which is capable of shielding one or more dental handpieces and sharp instruments inserted in the handpieces, to prevent inadvertent piercing injury and/or viral transmission due to accidental contact with the dental instrument or instruments.

Yet another object of this invention is to provide a new and improved curved, transparent and adjustable dental instrument shield for protecting the dental hygienist, assistant, dentist and patient from accidental injury due to contact with various tools and equipment, including sharp dental instruments, which dental instrument shield is capable of being adjustably or permanently mounted on substantially any dental console or support.

Yet another object of this invention is to provide a multi-directionally adjustable shield which is characterized by a curved, opaque or transparent guard adjustably or fixedly mounted on a pair of upward-standing support rods, which support rods are either connected directly to a fixed object such as a dental console or to a support bar attached to the fixed object or console, wherein the shield extends forwardly of or over one or more dental handpieces or other tool or tools or equipment and the sharp dental instruments projecting from the handpieces, to guard the dental instruments from accidental contact by an operator, including a dentist, dental assistant or hygienist and patient.

SUMMARY OF THE INVENTION

These and other objects of the invention are provided in a new and improved multi-directionally adjustable dental instrument shield which is characterized by a curved, transparent guard adapted to extend over one or more dental instruments located in dental handpieces and support members attached to the guard in adjustable relationship for mounting the guard on a dental console or other support. In a preferred embodiment, a dental tray is adjustably mounted on the guard to locate various dental instruments in close proximity to the dentist or dental assistant and specially designed instrument clips receive the various dental handpieces for location beneath the guard.

BRIEF DESCRIPTION OF THE DRAWINGS

The invention will be better understood by reference to the accompanying drawings, wherein:

FIG. 1 is a perspective view of a preferred embodiment of the dental instrument shield of this invention;

FIG. 2 is a perspective view of an alternative preferred embodiment of the dental instrument shield, wherein the guard element is mounted directly on a dental console;

FIG. 3 is a perspective view of a third preferred embodiment of the dental instrument shield of this invention, also mounted on a dental console;

FIG. 4 is a perspective view of a universal bracket for securing the dental instrument shield on a dental console in an alternative mounting configuration;

FIG. 5 is an alternative stud button bracket for securing the dental instrument shield to a console;

FIG. 6 is a side view of the universal bracket illustrated in FIG. 4, in mounted configuration;

FIG. 7 is a perspective view of yet another preferred embodiment of the dental instrument shield of this invention;

FIG. 8 is a side view, partially in section, of the dental instrument shield illustrated in FIG. 7;

FIG. 9 is a perspective, exploded view of a preferred handpiece mount for use with the dental instrument shield of this invention;

FIG. 10 is a sectional view, taken along line 10—10, of the handpiece mount illustrated in FIG. 9;

FIG. 11 is a perspective view of a mounting wedge used to orient the guard element of the dental instrument shield at a desired attitude;

FIG. 12 is a side view of a first preferred technique for mounting the guard element in a forward-leaning configuration using a pair of mounting wedges illustrated in FIG. 11; and FIG. 13 is a side view of a second preferred technique for mounting the guard element in a rearward-leaning configuration using a pair of the mounting wedges illustrated in FIG. 11.

DESCRIPTION OF THE PREFERRED EMBODIMENTS

Referring initially to FIG. 1 of the drawings, in a first preferred embodiment of the invention the dental instrument shield of this invention is generally illustrated by reference numeral 1. The dental instrument shield 1 includes a front-to-rear curved guard 2, having a rear segment 3 extending from a rear segment edge 4 and curving upwardly to define a top segment 5 and subsequently downwardly, to define a front segment 6, which terminates in a front segment edge 7. An instrument tray 11 is optionally mounted on the curved guard 2 by means of a pair of spaced tray supports 8, one of which is illustrated in FIG. 1. Each of the tray supports 8 is characterized by a tray support slot 9, which engages the outer curved edge of the curved guard 2 near the top segment 5, respectively, to facilitate slidable movement of the instrument tray 11 along the outside edges of the curved guard 2. In a first preferred embodiment, the instrument tray 11 is attached to the tray supports 8 by means of tray legs 12, illustrated in phantom, which are inserted in corresponding seats (not illustrated) provided in the tray supports 8. The rear segment edge 4 and the bottom portion of the rear segment 3 of the curved guard 2 are inserted in vertically-oriented mount block slots 14, provided in a pair of spaced guard mount blocks 13, as further illustrated in FIG. 1, in order to support the curved guard 2 in the illustrated configuration. The horizontal legs 18 of a pair of spaced support rods 16 project through a horizontal opening (not illustrated) provided in each of the the guard mount blocks 13 and each support rod 16 is shaped to define a support rod bend 17 and a vertical leg 19 projecting downwardly from the support rod bend 17. Each vertical leg 19 projects from a corresponding support rod bend 17 in spaced relationship downwardly through a vertical opening (not illustrated) provided in each one of a pair of spaced support rod mounts 20, one of which is illustrated in FIG. 1. Each of the support rod mounts 20 is provided with a horizontal rod mount slot 21, for receiving the frontal bar segment 25 of a horizontal instrument support bar 23. The instrument support bar 23 is further characterized by spaced support bar bends 24, one of which is illustrated in FIG. 1, and rear bar segments 26 extend from the support bar bends 24 and are secured to a dental console or other support (not illustrated). Three handpiece receptacles 27 are mounted in sliding spaced relationship on the frontal bar segment 25 of the instrument support bar 23 and are each provided with a vertical receptacle mount slot 28 for receiving a separate conventional handpiece 29. Each handpiece 29 is fitted with a handpiece grip 30, having a connecting cord 31 extending from the base thereof and a dental instrument 32 is attached to the opposite end of two of the handpieces 29. The third handpiece 29 is fitted with a nozzle 22, for irrigating the mouth during the various dental procedures. As heretofore described, the rear bar segments 26 which extend rearwardly in spaced, parallel relationship beneath the curved guard 2, may be fitted with a variety of fittings, brackets or other connecting implements (not illustrated) to secure the dental instrument shield 1 to a dental console or alternative support (not illustrated), according to the knowledge of those skilled in the art.

Referring now to FIG. 2 of the drawings, in another preferred embodiment of the invention the curved guard 2 is mounted directly to the console flange 33a of a conventional dental instrument console 33, by means of a pair of slot bolts 2b, which extend through vertical, parallel, spaced guard slots 2a, located in the rear segment 3 of the curved guard 2. In a preferred embodiment, a washer 2c is located between the bolt head of each slot bolt 2b and the guard slot 2a as illustrated, to facilitate a more secure, yet vertically-adjustable mount in each of the guard slots 2a. In the embodiment illustrated in FIG. 2, the curved guard 2 is designed to partially enclose a handpiece 29 which is seated in the receptacle mount slot 28 of a handpiece receptacle 27, secured directly to the instrument console 33. Accordingly, it will be recognized by those skilled in the art that under circumstances where one or more handpieces 29 are mounted in the handpiece receptacles 27 located directly on the instrument console 33, the curved guard 2 may be installed such that the front segment 6 and front segment edge 7 of the curved guard 2 project forwardly of the dental instrument 32, mounted in the top end of the handpiece 29, in order to protect the dentist, dental technician or assistant and patient from inadvertently contacting the dental instrument 32.

Referring now to FIG. 3 of the drawings, in yet another preferred embodiment of the invention the dental instrument shield 1 is characterized by a curved guard 2 mounted in a pair of spaced guard mount blocks 13, as illustrated in FIG. 1. However, the spaced, downwardly-extending vertical legs 19 are each seated in an opening (not illustrated) provided in a bracket pin 35, located in a console bracket 34, wherein a bracket pin mount 36 carries the bracket pin 35 and secures the bracket pin 35 to the sides, respectively, of an instrument console 33. An allen screw 38 may be threadably seated in the console bracket 34 for contacting the vertical legs 19 and facilitating vertical adjustment of the support rods 16 and the curved guard 2, as deemed necessary. Similarly, referring again to FIGS. 1 and 3 of the drawings, allen screws 38 may also be provided in the respective guard mount blocks 13, as hereinafter further described, to facilitate tightening of the guard mount blocks 13 on the horizontal legs 18 of the support rods 16. This feature allows pivotal adjustment of the curved guard 2 with respect to the support rod 16, as further hereinafter described. Referring again to FIG. 3 of the drawing, the conventional instrument console 33 is provided with vertically spaced console slots 33b, which are designed to receive and seat various handpieces 29 for access by the dentist or dental technician. Accordingly, the curved guard 2 is mounted on the instrument console 33 such that the front segment 6 and front segment edge 7 may be pivoted downwardly over the dental instrument 32 mounted in the handpiece 29, to protect the dentist, dental technician or assistant and patient from contact with the dental instrument 32.

Referring now to FIGS. 4 and 6 of the drawings, in yet another preferred embodiment of the invention the curved guard 2 may be mounted directly to an instrument console 33 by means of a universal bracket 39. The universal bracket 39 is characterized by a slot leg 40, fitted with a bracket slot 41 and a stud leg 42, projecting from the slot leg 40 in 90 degree relationship, as illustrated. A threaded stud 43 projects outwardly from the stud leg 42 and is designed to receive a lock nut 44, as illustrated in FIG. 6, after extension through an opening 10, provided in the rear segment 3 of the curved guard 2, to secure the curved guard 2 to the stud leg 42. The slot leg 40 of one or more universal brackets 39 can then be mounted to the instrument console 33 in a desired location using suitable fasteners (not illustrated), as further illustrated in FIG. 6, to position the curved guard 2 over one or more handpieces 29 (not illustrated).

Referring now to FIG. 5 of the drawings, in yet another preferred embodiment of the invention one or more stud buttons 45 can be used to secure the curved guard 2 directly to an instrument console 33. Each stud button 45 is characterized by a button base 45a, fitted with an adhesive 46 on the bottom thereof and having a threaded stud 43 projecting from the opposite side of the button base 45a. Accordingly, the adhesive 46 can be attached to a dental console or other support (not illustrated) in a desired location and the threaded stud 43 projected through the opening 10, located in the rear segment 3 of the curved guard 2, in the same manner as illustrated in FIG. 6. A lock nut 44 is then threaded on the stud 43, in order to secure the curved guard 2 on the stud buttons 45.

Referring now to FIGS. 11-13 of the drawings, the attitude of the curved guard 2 may be adjusted when the curved guard 2 is mounted directly to the instrument console 33, by using two pairs of mounting wedges 47, each of which is characterized by a tapered wedge face 48, a wedge base 49 and a fastener opening 50. Accordingly, as illustrated in FIGS. 12 and 13, under circumstances where the rear segment 3 of the curved guard 2 is attached directly to an instrument console 33 using the slot bolts 2b, illustrated in FIG. 2, the universal bracket 39, illustrated in FIGS. 4 and 6, or the stud buttons 45, illustrated in FIG. 5, as well as any other fastener, the curved guard 2 may be tilted forwardly or rearwardly. For example, as illustrated in FIG. 12, a pair of mounting wedges 47 may be oriented as illustrated to tilt the curved guard 2 forwardly with respect to a dental instrument console or other support (not illustrated). Alternatively, as illustrated in FIG. 13, the position of the respective pairs of mounting wedges 47 may be reversed, in order to tilt the curved guard 2 rearwardly with respect to the console (not illustrated).

Referring now to FIGS. 9 and 10 of the drawings, in a most preferred embodiment of the invention a tapered clip plug 60 is designed to seat in a conventional tapered handpiece receptacle 62, which may be mounted on the frontal bar segment 25 of the instrument support bar 23 illustrated in FIG. 1, to facilitate relocation of the various handpieces 29 without removing the respective handpieces 29 from each clip plug 60. Accordingly, each of the clip plugs 60 is characterized by an instrument clip 51, having a clip base 52 which is secured to the clip plug 20 by means of a clip bolt 55 and fitted with extending sets of clip fingers 53. Each of the clip fingers 53 is separated from a corresponding adjacent clip finger 53 by means of a finger slot 54 and the clip fingers 53 are designed to removably engage and clamp the handpieces 29, respectively, such that the handpieces 29 can be quickly and easily inserted in and removed from the instrument clip 51. The clip fingers 53 are designed to engage a tapered handpiece 29, such that each of the clip fingers 53 conform to the varying diameter of the handpiece 29, in order to better secure the handpiece 29 in the instrument clip 51. Accordingly, the finger slot 54 allows each of the clip fingers 53 to operate independently of each other and conform to the varying diameter under circumstances where the handpieces 29 are tapered at the point where they engage the instrument clip 51. As illustrated in FIG. 10, each of the conventional tapered handpiece receptacles 62 is provided with a receptacle mount flange 63, having a mount flange opening 64, for accommodating the frontal bar segment 25 of the instrument support bar 23 and mounting the various tapered handpiece receptacle 62 in spaced relationship on the instrument support bar 23, as illustrated in FIG. 1.

Referring now to FIGS. 7 and 8 of the drawings, in yet another preferred embodiment of the invention a hood 56 is designed to partially enclose a single handpiece 29 and is characterized by a pair of parallel side plates 57, connected by a curved top 58 and provided with a rear plate 59, which spans the side plates 57. Accordingly, the hood 56 is closed on three sides and open on the front and at the bottom to effect easy removal of the handpiece 29 and insertion of the handpiece 29 in an instrument clip 51, secured to a handpiece receptacle 27. Alternatively, the instrument clip 51 may be attached to a clip plug 60, which is adapted for insertion in a conventional tapered handpiece receptacle 62, as illustrated in FIGS. 9 and 10. As in the case of the dental instrument shield 1 illustrated in FIG. 1, the bottom edge of the rear plate 59 of the hood 56 is slidably inserted in the mount block slot 14 of a guard mount block 13, which guard mount block 13 is pivotally mounted on a vertically-oriented support rod 16 by means of an allen screw 38. The bottom end of the support rod 16 is similarly attached to the handpiece receptacle 27, which handpiece receptacle 27 is, in turn, secured to the frontal bar segment 25 of the instrument support bar 23. Accordingly, the handpiece 29, illustrated in phantom and carrying a dental instrument 32, is seated in the instrument clip 51 such that the dental instrument 32 is shielded within the hood 56. Inadvertent contact between the dentist, dental assistant or technician or the patient with the dental instrument 32 is therefore prevented.

Referring again to FIG. 1 of the drawings, it will be appreciated by those skilled in the art that the curved guard 2 of the dental shield instrument 1 is highly versatile, in that it can be adjusted in substantially any direction to accommodate and shield the various sharp dental instruments 32 mounted on the ends of the respective handpieces 29. For example, each of the guard mount blocks 13 may be pivoted forwardly or rearwardly to also pivot the curved guard 2 and extend the front segment 6 and front segment edge 7 further downwardly or upwardly as desired, and protect the dentist, dental assistant or technician and the patient from the dental instruments 32. Furthermore, the curved guard 2 can be slidably adjusted either to the right or left in the respective mount block slots 14 and the curved guard 2 may be raised or lowered by sliding the vertical legs 19 in the spaced support rod mounts 20. Pivotal adjustment of the curved guard 2 on the horizontal legs 18 of the support rod 16 may require manipulation of the respective allen screws (not illustrated) seated in the guard mount blocks 13, to loosen the connections between the respective guard mount blocks 13 and the horizontal legs 18. Similarly, vertical adjustment of the curved guard 2 may require loosening other allen screws (not illustrated) provided in each of the support rod mounts 20. As heretofore described, the instrument tray 11 is slidably adjusted on the outside edges of the curved guard 2 to allow tilting of the instrument tray 11 forwardly toward the dentist or away from the dentist, as desired. The curved guard 2 may also be tilted forwardly and rearwardly by rotating the support rod mounts 20 on the frontal bar segment 25 of the instrument support bar 23. Moreover, the respective handpiece receptacles 27 may also be fitted with allen screws (not illustrated), to facilitate slidable adjustment of the handpiece receptacles 27 on the frontal bar segment 25. It is understood that various alternative frictional locking mechanisms, such as thumb screws, clamps of various design and like devices can be used instead of the allen screws to facilitate adjustment of the handpiece receptacles 27 on the frontal bar segments 25.

Referring again to FIG. 2 of the drawings, the curved guard 2 is rendered vertically adjustable with respect to the instrument console 33 by loosening the respective slot bolts 2b and adjusting the curved guard 2 vertically, utilizing the respective parallel guard slots 2a.

As illustrated in FIG. 3 of the drawings, pivotal and slidable adjustment of the curved guard 2 is facilitated by operation of the respective guard mount blocks 13 in the same manner as illustrated in FIG. 1. Furthermore, the curved guard 2 and the support rod 16 can be pivoted forwardly or rearwardly with respect to the instrument console 33 by operation of the bracket pin 35, which is pivotally mounted in the bracket pin mount 36. Vertical adjustment of the curved guard 2 is also facilitated by loosening the respective allen screws 38, located in the bracket pins 35, and making the desired adjustment.

Referring again to FIGS. 7 and 8 of the drawing, under circumstances where the hood 56 is used to guard a single dental instrument 32 located in the corresponding handpiece 29, the hood 56 can be slidably adjusted from side to side in the mount block 14 of the guard mount block 13 in the same manner as heretofore described with respect to the dental instrument shield 1 illustrated in FIGS. 1 and 3. Vertical and pivotal adjustment is also achieved in the same manner by adjusting the allen screw 38, threaded in the guard mount block 13, or manipulating another allen screw 38 provided in the handpiece receptacle 27. Furthermore, the hood 56 can be tilted forwardly or rearwardly with respect to the dental instrument 32 and the handpiece 29, by pivoting the handpiece receptacle 27 on the frontal bar segment 25 of the instrument support bar 23.

Referring again to FIG. 1 of the drawing, it will be appreciated that various modifications can be made in the mounting apparatus which supports the curved guard 2. For example, horizontal slots (not illustrated) can be provided in the support rod mounts 20 and the rear segment edge 4 of the curved guard 2 seated in these slots, thereby eliminating the necessity for the guard mount blocks 13 and support rods 16. Furthermore, referring to FIGS. 1, 9 and 10, the handpiece receptacles 27 and the clip plugs 60 can be drilled or otherwise altered to receive the vertical legs 19 of the support rods 16 and eliminate the need for the support rod mounts 20. Moreover, the curved guard 2 can be modified to be incorporated directly into the design of any working surface to project over various tools and instruments.

It will be appreciated by those skilled in the art that the dental instrument shield of this invention, in its various embodiments, offers a versatile and effective means for protecting a dentist, dental assistant or hygienist, and patient, as well as any other occupant of the dental office, from injury and possible blood contamination due to inadvertent contact with a dental tool or instrument. The curved guard 2 and hood 56 are preferably characterized by a transparent, plastic plate material shaped in the desired configuration by techniques which are well known to those skilled in the art. The curved guard 2 and the hood 56 are designed to be mounted on substantially any support, including a dental console, regardless of configuration or location, and may be easily adapted to extend over one or more handpieces 29 for protective purposes. The clip plug 60 and instrument clip 51, illustrated in FIGS. 9 and 10, provide versatility in mounting handpieces 29 of varied design. Moreover, the instrument tray 11, illustrated in FIG. 1, may be constructed of an autoclavable material, including heat-resistant plastic formulations and stainless steel, in non-exclusive particular, such that both it and instruments located on it can be simultaneously sterilized. Other features such as sterilizing and disinfecting lights can also be attached to or placed on the dental instrument shield 1 and lights or light-emitting diodes may be incorporated on the dental shield 1, instrument clip 51, clip plug 60 or handpiece receptacle 27, illustrated in FIGS. 1 and 2, to indicate which handpieces 29 are in use, for additional safety.

While the dental instrument shield of this invention is designed primarily to protect a dentist, dental assistant and patient from unguarded dental instruments, it is understood that the shield can equally well be incorporated in any desired shape and material of construction, into an industrial or working environment where the risk of viral or micro-organism contamination is apparent. Thus, the shield may be used in shops and similar environments where many people work and body fluid contact is possible.

Accordingly, while the preferred embodiments of the invention have been described above, it will be recognized and understood that various modifications may be made in the invention and the appended claims are intended to cover all such modifications which may fall within the spirit and scope of the invention.

Having described my invention with the particularity set forth above, what is claimed is:

1. A dental instrument shield for shielding at least one dental instrument mounted on an instrument support, said dental instrument shield comprising a substantially transparent guard disposed at least partially over the dental instrument; at least one guard mount block having a mount block slot for slidably receiving one edge of said guard; at least one support rod pivotally supporting said guard mount block; and at least one support rod mount attached to said instrument support in pivotal relationship and receiving said support rod, for pivotally mounting said dental instrument shield on said instrument support.

2. The dental instrument shield of claim 1 further comprising a dental console and at least one console bracket provided on the dental console and adapted for engaging said instrument support and mounting said instrument support and said dental instrument shield on the dental console.

3. The dental instrument shield of claim 2 wherein said console bracket further comprises a universal bracket.

4. The dental instrument shield of claim 1 wherein said guard is curved from front to rear and the front edge of said guard terminates in spaced relationship with respect to the dental instrument.

5. The dental instrument shield of claim 1 wherein the dental instrument further comprises a single dental instrument and said guard further comprises a hood for substantially enclosing the single dental instrument.

6. The dental instrument shield of claim 5 further comprising a rear panel closing the rear of said hood, wherein the front and bottom of said hood remain open for accessing the dental instrument.

7. The dental instrument shield of claim 5 wherein said hood is transparent.

8. The dental instrument shield of claim 1 further comprising at least one handpiece receptacle provided on said instrument support for removably receiving a dental handpiece carrying the dental instrument.

9. The dental instrument shield of claim 8 further comprising a dental console and a console bracket provided on the dental console and adapted for engaging said instrument support and mounting said instrument support and said dental instrument shield on the dental console.

10. The dental instrument shield of claim 9 wherein said guard is transparent and curved from front to rear and the front edge of said guard terminates in spaced relationship with respect to the dental instrument.

11. The dental instrument shield of claim 8 further comprising clip means provided on said handpiece receptacle for removably engaging and retaining the dental handpiece.

12. The dental instrument shield of claim 11
further comprising a dental console and a console bracket provided on the dental console and adapted for engaging said instrument support and mounting said instruments support and said dental instrument shield on the dental console and wherein
said guard is transparent and curved from front to rear and the front edge of said guard terminates in spaced relationship with respect to the dental instrument.

13. The dental instrument shield of claim 11 wherein said clip means further comprises a clip plug shaped to removably engage said handpiece receptacle and a clip mounted on said handpiece receptacle, said clip having two sets of oppositely-disposed clip fingers for removably engaging and retaining the dental handpiece.

14. The dental instrument of claim 13
further comprising a dental console and a console bracket provided on the dental console and adapted for engaging said instrument support and mounting said instrument support and said dental instrument shield on the dental console and wherein
said guard is transparent and curved from front to rear and the front edge of said guard terminates in spaced relationship with respect to the dental instrument.

15. A dental instrument shield for mounting on a dental instrument console and shielding at least one dental instrument, said dental instrument shield comprising a guard disposed at least partially over the dental instrument in shielding relationship; a pair of guard mount blocks, each having a mount block slot for slidably receiving one edge of the guard in spaced relationship; a pair of support rods pivotally carried by said guard mount blocks in spaced, vertical relationship; a pair of support rod mounts pivotally attached to said support rods in spaced relationship beneath said guard mount blocks, respectively; an instrument support bar pivotally carried by said support rod mounts in horizontal orientation; and mounting means provided on the ends of said instrument support bar for mounting said instrument support bar on the dental instrument console.

16. The dental instrument shield of claim 15 wherein said mounting means further comprises at least one console bracket provided on the console for engaging said ends of said instrument support bar and mounting said instrument support bar on the console.

17. The dental instrument shield of claim 15 wherein said mounting means further comprises at least one universal bracket.

18. The dental instrument shield of claim 15 wherein said mounting means further comprises at least one stud button.

19. The dental instrument shield of claim 15 wherein said guard is transparent and curved from front to rear and the front edge of said guard terminates in spaced relationship with respect to the dental instrument.

20. A dental instrument shield for mounting on a dental instrument console and shielding at least one dental instrument, said dental instrument shield comprising a guard disposed at least partially over the dental instrument in shielding relationship; a pair of slots vertically disposed in said guard in spaced relationship and fastening means adapted to extend through said slots and into the dental instrument console for securing said guard on the dental instrument console and wedge means disposed on at least one side of said guard for tilting said guard in a selected direction.

* * * * *